United States Patent [19]
Torikai et al.

[11] Patent Number: 5,959,176
[45] Date of Patent: Sep. 28, 1999

[54] PLANT PROMOTER AND UTILIZATION THEREOF

[75] Inventors: Satomi Torikai, Toyonaka; Kenji Oeda, Kyoto, both of Japan

[73] Assignee: Sumitomo Chemical Company, Limited, Osaka, Japan

[21] Appl. No.: 08/911,434

[22] Filed: Aug. 12, 1997

[30] Foreign Application Priority Data

Aug. 12, 1996 [JP] Japan .................................. 8-212680

[51] Int. Cl.⁶ .............................. A01H 5/00; C12N 5/04; C12N 15/29; C12N 15/82
[52] U.S. Cl. ......................... 800/287; 800/278; 800/298; 435/69.1; 435/320.1; 435/419; 435/468; 536/23.6; 536/24.1
[58] Field of Search ............................ 435/172–3, 320–1, 435/419, 468, 69.1; 536/23.1, 24.1, 23.6; 800/205, 278, 287, 298

[56] References Cited

FOREIGN PATENT DOCUMENTS

| | | |
|---|---|---|
| 0452269A2 | 10/1991 | European Pat. Off. . |
| 0659884A2 | 6/1995 | European Pat. Off. . |
| WO9113992 | 9/1991 | WIPO . |
| WO9402619 | 2/1994 | WIPO . |

OTHER PUBLICATIONS

Fraile et al. A century of tobamovirus evolution in an Australian population of Nicotiana glauca. Journal of Virology. 71(11):8316–8320, Nov. 1997.

Lin, Xiaoying. *Plant Physiology*; vol. 112, No. 3, 1996, pp. 1365–1374.

Hoffmann–Sommergruber, K.. "Molecular characterization of Dau C1 the major allergen from carrot, AC Z81362." EMBL Database, Jun. 1, 1997, Heidelberg, XP002064206.

Yamamoto, Mika et al. *Plant Cell Physiology*; vol. 38, No. 9, Sep. 1997, pp. 1080–1086.

Yamamoto et al. (1990) *Nucleic Acids Research*, vol. 18, No. 24, p. 2449.

Ebener et al.(1993) *Plant Physiol.* 101:259–265.

*Primary Examiner*—David T. Fox
*Attorney, Agent, or Firm*—Birch, Stewart, Kolasch & Birch, LLP

[57] ABSTRACT

There is disclosed a plant promoter which is functional in plant cells comprising a nucleotide sequence (about 250 bp) of SEQ ID NO: 1 and use thereof.

21 Claims, 10 Drawing Sheets

FIG. 3

```
CR16C1(Carrot)    1: MGAQSHSLEITSSVSAEKIFSGIVLDVDTVIPKAAPGAYKSV-DVKGDGAG——TVRIIITLPEGSPITSMTVRTDAVNKEALTYDSTVIDGDILLEFIE 96
AplgI(Celery)     1: ..V.T.V..L.......Q.F.I......L......-EI......P..—LK....D.G..T.L.I.G......F.YS........G.... 96
PcPR1-3(Parsley)  1: ..V.KSEV.A......L.K.LC..I..LL.RVL...I..SETLE....V..—.....KLVH.GDA..FKT.KQKV..ID.ATF..SYSI......G... 97
Betv1(Birch)      1: .VFNYET.T..VIP.ARL.KAFI..G.NLF.V..Q.IS..ENIE.N..P.—IKK.SF....F.FKYYKD.V.E.DHTNFK.NYS...E.GPIGDTL. 97
Cora1(Hazel)      1: .VFNYEV.TP.VIP.ARL.KSY...G.KL...V..Q.IT..EN.E.N..P.—IKN..FG....RYKYYKE.V.E.DNTNF..SY...E..V.GDKL. 97
Mald1(Apple)      1: ..VYTFEN.F..EIPPSRL.KAF...A.N...I...Q.I.QAEILE.N..P.—IKK..FG....QYGYYKH.I.SIDEASYS.SY.L.E..A.TDT.. 97
STH-2(Potato)     1: ..VT.YTH.T.TPIAPTRL.KAL.V.S.N....LM.Q-V.—NI-EAE.D-—SIKKANFV.....KYLKHKIHV.DDKN.VTKYSM.E..V.GDKL. 92
PvPR1(Bean)       1: ..VFTFEDQT..P.APATLYKAVAK.A..IF...L.DSF....EI.E.N..P.—IKK.SFV.DGETKFVLHKIESIDEAN.G.SYSIVG.VA.P.TA. 97
SAM22(Soybean)    1: ..VFTFED..N.P.APATLYKAL.T.A.N.....L-DSF....EN.E.N..P.—IKK..FL.DGETKFVLHKIESIDEAN.G.SYS.VG.AA.PDTA. 96
Pl49(Pea)         1: ..VFNVED.....V..APAILYKAL.T.A.NLT..VI-D.I..IEI.E.N......—IKKL.FV.DGETKMLHKVEL.DVAN.A.NYSIVG.VGFPDTV. 96
ABR17(Pea)        1: .VFVFDD.YV.T.APP.LYKALAK.A.EIV.-KVIKEAQG.EIIE.N..P.TI—KKLSIL.DGKTNYLHKL...DEANFG.NYSLVG.PG.H.SL. 96
AoPR1(Asparagus)  1: .SSG.W.H.VAVN.A.GRM.KAAM..WHNLG..IV.DFIAGGSV.S...SV.TIREIK.N-N.AIPFSYVKERLDFVDHDKFEVKQTL.EG.G-.GKMF. 98
PBZ1(Rice)        1: .APACV.D.HAVA....RLWK-AFM.AS.L-...CA.LV-DDIA.E.N..P.TIY.MKLNPAAGVGSTY-K.RVAVCDAASHVLKSDVLEAESKVGKL-K 95
                                  *                                *       *                       *             **

CR16C1(Carrot)    97: SIETHMWVPTADGGSITKTAIFHTKGDAVVPEENIKFADAQNTALFKAIEAYLIAN—— 154
AplgI(Celery)     97: ...N.V.L................C..........Y.NE..........L.......V............... 154
PcPR1-3(Parsley)  98: ..NN.FTA..N....CTV.S.I..N................ND..LTI...V............ 155
Betv1(Birch)      98: K.SNEIKI..A.P.......L..ISNKY......HE.KA.QV.ASKEMGET.LR.V.S..L.HSDAYN 160
Cora1(Hazel)      98: KVCHELKI.AAPG.....L..ISSK..A....HEINA.EM.G.KEMAEK.LR.V.T..L.HSAEYN 160
Mald1(Apple)      98: K.SYETKL.ACGS.ST.-.SISHY.....NIEIK..HV.VGKEKAHG....L..S..KDHPDAYN 159
STH-2(Potato)     93: ..SYDLKFEAHGN..CVC.SITEY......Y.LKD.EHNEGQK.GME....IV......L..PSYYA 155
PvPR1(Bean)       98: K.TFDSKLSDGPN...LI.LSITY.S.....PPN.DEL.AGK.KSDS....V.....L..P——— 156
SAM22(Soybean)    97: K.TFDSKL.AGPN....AG.L.VKYE.....EPNQDEL.TGK.KAD............L.HP-DYN 158
Pl49(Pea)         97: K.SFEAKLSAGPN.....A.LSVKYF......APS..QL.TDK.KGDG......L.G.CL.HP-DYN 158
ABR17(Pea)        97: KVAFETIILAGS......V..ISVKY........ALSDAVRDETK.KG.G.I......G.-VLANPGY- 157
AoPR1(Asparagus)  99: CAT..FKFE.SSN..CLV.V..SYKILPGVADESAKA..EGITN-H-N—..T....L..PTAYV 158
PBZ1(Rice)        96: .HS.ETKLEA.G..SCVA.LKVEYELEDGSSLSP..KE.DIVDGYYGML.M..D..V..HPAEYA 158
                                                                              **
```

■ Non-stained region
□ Stained region

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 247 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Daucus carota L.
      (C) INDIVIDUAL ISOLATE: Kuroda Gosun (ix) FEATURE:
      (A) NAME/KEY: promoter
      (B) LOCATION: 1..247

(xi) SEQUENCE DESCRIPTION: SEQ ID NO:1:

```
TTCTAGAATA TATCTTTTGA AATTTCAACA AACACAGCAC TAACTTTTCT TTTAACAGAT      60

TAGAATCGTT TCCTAAACTT TTAAAATTAA AAAATACATT ACTATAATAT TTATCAACAC     120

CTCAACATTC ATGTTAGCGT ACTATAAATA GGTGCTCTTG GTGCTCTACT ATCATCACAT     180

CAATCTTCCA GCACAAACCT TGAGCTTAAT CTTTCTACTA ATTTTTAGCA AAAACATTCT     240

AAAGGTC                                                              247
```

(2) INFORMATION FOR SEQ ID NO:2:

(i) SEQUENCE CHARACTERISTICS:
      (A) LENGTH: 2042 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Daucus carota L.
      (C) INDIVIDUAL ISOLATE: Kuroda Gosun (ix) FEATURE:
      (A) NAME/KEY: promoter
      (B) LOCATION: 1..2042

(xi) SEQUENCE DESCRIPTION: SEQ ID NO:2:

```
TCTCGGGCCA CTTTCAAGGA TAAAAGCACC GGGAAGAACG AGAAATCCGT AGTTCCGTGG      60

AATTGAGATC TAAGAAAAGA AGGCCAAATC GGAAAAGGTT TTGAATCCTT AGATCCGGAA     120

AAACAAATGC CAAAGAAGTT TTATTGGAAG AAAAAAGCAA ACACAAAAGA AGAGAAATAA     180

AAAATTTTGG GGCTTTCCAC CGGTAATGGA AGAATATGCA CAAAAATTCA CGCCAACAGA     240

GTCCTTACTT AACTCTCACC TTTTGCACAC TCTTTCTCAT ATTTTTTTTT ATCTTTTTGT     300

TCAAAAAATT TGAATATAAT ATAATAATAA TAATAATAAT AATAATAATA ATAATAATAA     360

TAATAATAAT AATAATAATA ATAATAATAA TAATAATAAT AGGGAAGGCA AATAGGGATC     420

ATTGTTCGAG TTGTCAATCA ATACGGAGTC AATTGAAGTG TTATATATTT AGGATACCTT     480

CTTATTACAC AGCTGGAGAT GTTCTAGTCT ATCGAACTTA AAATTCCTCC AAATACAAAA     540

TATTTCTTAT GAAGAGCATC AACAGAATAA TTTCCAACTA ACACCCAATC GAGAAAGAGA     600

TTGATGCTTA TTGCCCAGTT TGTAATGCTG AAGCAGAGAC TACTCTTCAT GCGTTCGTTA     660

CACCTCATCA GTTCGCTAAT TACAAGACTT ATTGGGATAG TGTTGAGAGT CTAATTACAG     720

CTACAGAGCA TGCTTCCTTT TTAGAATGGT TGAGCAATAC TTTCAACCAG GTGAAGAGTT     780

AAATCGGAGG GTAATGCTAA GTTGGGCCCT ATGGAAGAAC TGAAATGAGT TAGTGTGGCA     840

CCAAAGTATT ATGGAAATTA CAGGGGTGAC ATGTCTGCAC AACGGGCCCT TATACAACAC     900

TTTGGGCATG TTTGGGAAAG ACAGCTTATG GCTTTTTTTA TAAAGAGTCA GCTTCTACTT     960

CTCTTGACCC GTTTGTGTAA AAGGTTAGAA GCACTTAAAA AAAACCGACA ATACTAACTT    1020

TAGTTTCACG ACTTCTGCTT CTTTCCCAAA CAATTTAATC ACTTATAAAT CTTAATTTAC    1080

TTCTTACTTC TGGTGCACTT CTTTACTTTA TGCAAGAGAC ACTTTTTTTA AGTTTAACCA    1140

AACGACCCTT TCTCATCCCT TGTTCGAGTA GTCGAAGAAT GCAAAGAGAA GTAAGAATCA    1200

GCAGGTGTCA CTACAGTTTG CAAAATGACA CGCAAATAAA GTAGCCCACC GCTCAGTGAG    1260

ATATTGATTC TACCATTGAT CGTGTTTGGT GTGTAGATGA TGCACACATG GACTTCATTC    1320

ACGTAATGTT GAACGATTTG ATAAATTAGT GAAATTTCAT TTCTTGGGCA AAAAAAGTCC    1380

CAAAGTCTAT ATAGGTTCTA AGTGAAACCA ACTCCTAAAT TATACAGCTA AATTGAGCAT    1440

CAGTGGAATC CATCTTCTCA ATTATAAATG CAAATAGAAT TAGTACATAT AACTAGAATT    1500

TAAATTAACA TATGTAATTC ATGTAACGGT CTACATCGCA TGAAATTATT TATCTGAATG    1560

ATAACATCTT TGTAAACAAA ACTGGGCCAA ATAGGACCAT AACCAAGTTC ACGTGTATTC    1620

TAAAATGTTA ATACTAACAT GAGTATTTTC TTTTCAAGGT ATAAGTTAAT TCTTCAATCA    1680

ATTAACTTTA AATTTGGACA TTATTGAGCA ACTTTATGCC CACGTTGTAT TGTTTAAACA    1740

ACGTTTGTCC GGTGTATATT TATGACCTTT CAACTCAAGC TAGCCAGTGA ATGCTTTCTA    1800

GAATATATCT TTTGAAATTT CAACAAACAC AGCACTAACT TTTCTTTTAA CAGATTAGAA    1860

TCGTTTCCTA AACTTTTAAA ATTAAAAAAT ACATTACTAT AATATTTATC AACACCTCAA    1920

CATTCATGTT AGCGTACTAT AAATAGGTGC TCTTGGTGCT CTACTATCAT CACATCAATC    1980

TTCCAGCACA AACCTTGAGC TTAATCTTTC TACTAATTTT TAGCAAAAAC ATTCTAAAGG    2040

TC                                                                  2042
```

(2) INFORMATION FOR SEQ ID NO:3:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
    (A) ORGANISM: Daucus carota L.
    (C) INDIVIDUAL ISOLATE: Kuroda Gosun (ix) FEATURE:
    (A) NAME/KEY: CDS
    (B) LOCATION: join(1..183, 312..593)

(ix) FEATURE:
    (A) NAME/KEY: intron
    (B) LOCATION: 184..311

(xi) SEQUENCE DESCRIPTION: SEQ ID NO:3:

```
ATG GGT GCC CAG AGC CAT TCA CTC GAG ATC ACT TCT TCA GTC TCC GCA          48
Met Gly Ala Gln Ser His Ser Leu Glu Ile Thr Ser Ser Val Ser Ala
 1               5                  10                  15

GAG AAA ATA TTC AGC GGC ATT GTC CTT GAT GTT GAT ACA GTT ATC CCC          96
Glu Lys Ile Phe Ser Gly Ile Val Leu Asp Val Asp Thr Val Ile Pro
             20                  25                  30

AAG GCT GCC CCT GGA GCT TAC AAG AGT GTC GAT GTT AAA GGA GAT GGT         144
Lys Ala Ala Pro Gly Ala Tyr Lys Ser Val Asp Val Lys Gly Asp Gly
 35                  40                  45

GGA GCT GGA ACC GTC AGA ATT ATC ACC CTT CCC GAA GGT TAGTTATATA          193
Gly Ala Gly Thr Val Arg Ile Ile Thr Leu Pro Glu Gly
         50                  55                  60

TCTCACCCCA TCTTGTTGAT GTATCATTTC TGATACCATA TTAATTTGAG GGGATTATTT       253

CCCGACATTG TACAATTAAT AAATTTTTTG AATACATATA TAATTCTCTG CTGCAGGT         311

AGC CCG ATC ACC TCA ATG ACG GTT AGA ACT GAT GCA GTC AAC AAG GAG         359
Ser Pro Ile Thr Ser Met Thr Val Arg Thr Asp Ala Val Asn Lys Glu
             65                  70                  75

GCC TTG ACA TAC GAC TCC ACC GTT ATT GAT GGA GAC ATC CTT TTA GGC         407
Ala Leu Thr Tyr Asp Ser Thr Val Ile Asp Gly Asp Ile Leu Leu Gly
 80                  85                  90

TTC ATC GAA TCC ATT GAA ACC CAT CTT GTC GTT GTG CCA ACT GCT GAC         455
Phe Ile Glu Ser Ile Glu Thr His Leu Val Val Val Pro Thr Ala Asp
         95                 100                 105

GGG GGT AGC ATT ACC AAG ACC ACG GCC ATA TTC CAC ACT AAA GGT GAT         503
Gly Gly Ser Ile Thr Lys Thr Thr Ala Ile Phe His Thr Lys Gly Asp
110                 115                 120                 125

GCC GTC GTT CCT GAA GAG AAC ATC AAG TTT GCA GAT GCT CAG AAC ACC         551
Ala Val Val Pro Glu Glu Asn Ile Lys Phe Ala Asp Ala Gln Asn Thr
                130                 135                 140

GCT CTC TTC AAA GCT ATC GAG GCC TAC CTC ATT GCT AAC TAA                 593
Ala Leu Phe Lys Ala Ile Glu Ala Tyr Leu Ile Ala Asn *
             145                 150                 155
```

(2) INFORMATION FOR SEQ ID NO:4:

(i) SEQUENCE CHARACTERISTICS:
    (A) LENGTH: 154 amino acids
    (B) TYPE: amino acid
    (D) TOPOLOGY: linear (ii) MOLECULE TYPE: protein (xi) SEQUENCE DESCRIPTION: SEQ ID NO:4:

```
Met Gly Ala Gln Ser His Ser Leu Glu Ile Thr Ser Ser Val Ser Ala
 1               5                  10                  15

Glu Lys Ile Phe Ser Gly Ile Val Leu Asp Val Asp Thr Val Ile Pro
             20                  25                  30

Lys Ala Ala Pro Gly Ala Tyr Lys Ser Val Asp Val Lys Gly Asp Gly
```

```
        35                  40                  45
Gly Ala Gly Thr Val Arg Ile Ile Thr Leu Pro Glu Gly Ser Pro Ile
    50                  55                  60

Thr Ser Met Thr Val Arg Thr Asp Ala Val Asn Lys Glu Ala Leu Thr
65                  70                  75                  80

Tyr Asp Ser Thr Val Ile Asp Gly Asp Ile Leu Leu Gly Phe Ile Glu
                85                  90                  95

Ser Ile Glu Thr His Leu Val Val Pro Thr Ala Asp Gly Gly Ser
            100                 105                 110

Ile Thr Lys Thr Thr Ala Ile Phe His Thr Lys Gly Asp Ala Val Val
        115                 120                 125

Pro Glu Glu Asn Ile Lys Phe Ala Asp Ala Gln Asn Thr Ala Leu Phe
    130                 135                 140

Lys Ala Ile Glu Ala Tyr Leu Ile Ala Asn
145                 150                 155
```

(2) INFORMATION FOR SEQ ID NO:5:

(i) SEQUENCE CHARACTERISTICS:
    (A) LENGTH: 836 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (vi) ORIGINAL SOURCE:
    (A) ORGANISM: Daucus carota L.
    (C) INDIVIDUAL ISOLATE: Kuroda Gosun (ix) FEATURE:
    (A) NAME/KEY: terminator
    (B) LOCATION: 1..836

(xi) SEQUENCE DESCRIPTION: SEQ ID NO:5:

```
GCTGAACTTT CCACCGTGTT TTAATAATCT GTCGTTTTTA AATTTATGGG AAGAGCGCCA      60
AAGATGCCTC AACTTCATAA TTTTATGAGC GGGCGATAGA ATTGCAACTT TTTCTTTGTA     120
CTCTGTTTTA ATGAGCAATT TCATTTGGTA ACAATATGTG TAATCTTTTT AAATAAAATA     180
TAGTACCGAC ATTAATGTAA TCTTTCTGGA TCATCTGTGC TTTCATATGT TACTTATATT     240
TTTTAGTTAA AAATGTAATT CACTTGAACC TTAATGATAT ATAGGTCATC CCAATTAATT     300
AATTTCAAGT TTCGGTTTGA AATTAGAAAG AGTAAAGAAT TTGTAGTATG AACGATGAGT     360
CGATGACAGA AAAAAGAAGC TTGCAGTGTC CCAAAAAGAT AAATTTAATT ATTTCATTAA     420
GTGAGAATGA TAAGACTCAG TAAACCTCCT CAGTTAGTCC ATCCAACCCT TATAAGCCTG     480
ATAACTGGTG ATTAATTGTA ATGATGTTTT ATTACTATGG GGCAGTTTGG CTGGACTTAA     540
AAAAAGTGAC TTATTGCTTA AAATAAATAA GTAGATTATA AGTGAAAAGT TGATTTGGAC     600
TTATAAGTTA TTAAAAGTGT TTGAATATAT ATTGATTATA AGTGATAGAA GAAGCTAAAT     660
CCCCAAAATA AGCTAGGTTT CCTAACTTCT TTTTTGGGGC TTTTAAGCTT CAATATAAGT     720
GCTTCTCATA ATTAGCCAAA CACCTCCATT TAAGTAGAAG TCGACTTCTA TGTTAAAAAA     780
GCTCCGAAGT CGGTTTGCCA AACACCCCCT ATATGGGTCT ATTCTTGGCA TCTAGA        836
```

(2) INFORMATION FOR SEQ ID NO:6:

(i) SEQUENCE CHARACTERISTICS:
    (A) LENGTH: 20 base pairs
    (B) TYPE: nucleic acid (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:6:

GCTGAACTTT CCACCGTGTT                                           20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:7:

GACATCTCAT AGTTGAGACT C                                         21

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:8:

GTAAAACGAC GGCCAGT                                              17

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:9:

GGGCTAGCGA CCTTTAGAAT GTTTTTGC                                  28

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO

-continued (xi) SEQUENCE DESCRIPTION: SEQ ID NO:10:

TCACGGGTTG GGGTTTCTAC                                       20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:11:

TCTGCATCGG CGAACTGATC                                       20

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:12:

ACAAACACAG CACTAACTTT TC                                    22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:13:

ACATGTGGAG TGAAGAGTAT C                                     21

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(iii) HYPOTHETICAL: NO (xi) SEQUENCE DESCRIPTION: SEQ ID NO:14:

CATGCTTAAC GTAATTCAAC AG                                    22

PLANT PROMOTER AND UTILIZATION THEREOF

BACKGROUND OF THE INVENTION

1. Field of the Invention

The present invention relates to a plant promoter and utilization thereof.

2. Description of the Related Art

Cauliflower mosaic virus 35S promoter (hereinafter, referred to as 35S promoter) has been known as an effective promoter for non-tissue-specific expression of a desired protein gene in plant cells and has been widely used.

However, an effective promoter that enables tissue-specific expression, particularly in root, of a desired protein gene in order to produce desirably transformed plants has been desired.

SUMMARY OF THE INVENTION

Under the circumstances, the present inventors have conducted extensive researches and found a promoter capable of functioning in plant cells, which enables tissue-specific expression of a gene of interest in vascular bundles, particularly vascular bundles in the root of plants, thereby completing the present invention.

The present invention provides:

1. A promoter which is functional in plant cells, comprising a nucleotide sequence (about 250 bp) of SEQ ID NO: 1,
2. A plasmid comprising the promoter of SEQ ID NO: 1.
3. A gene coding for a protein having a molecular weight of 16 kD, having a nucleotide sequence encoding an amino acid sequence of SEQ ID NO: 4,
4. A gene coding for a protein having a molecular weight of 16 kD, having a nucleotide sequence of SEQ ID NO: 3, and
5. A terminator capable of functioning in plant cells comprising a nucleotide sequence of SEQ ID NO: 5.

BRIEF DESCRIPTION OF DRAWING

FIG. 3 shows a comparison between the amino acid sequence of the protein of the present invention and amino acid sequences of various proteins.

Figure 1:
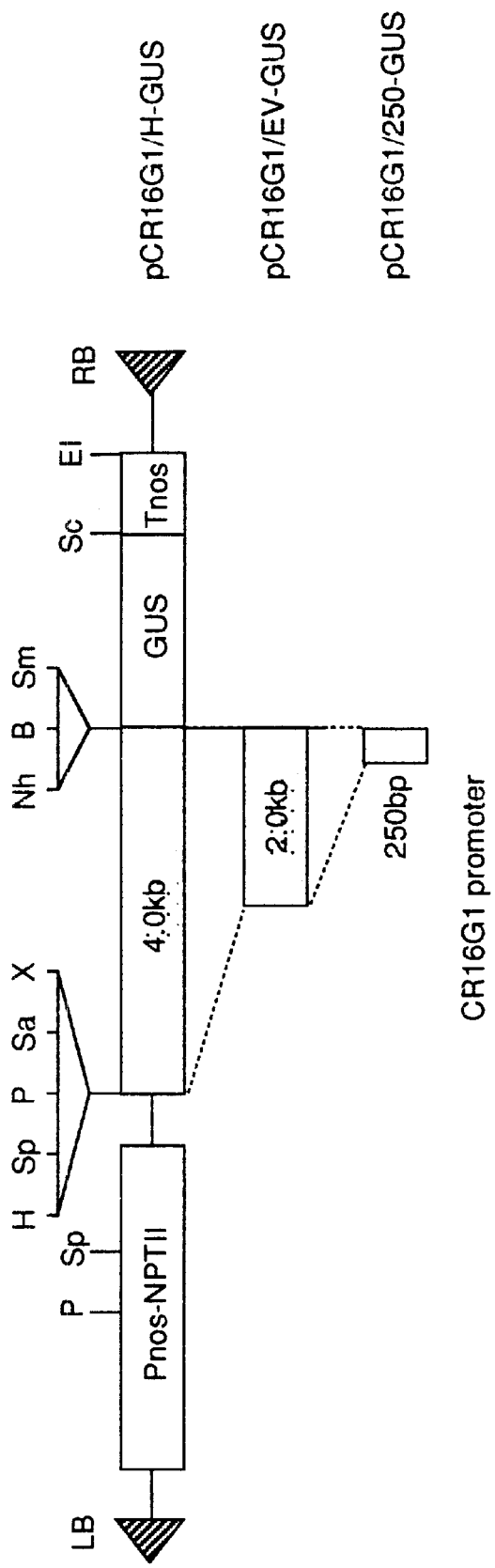
FIG. 1 shows pCR16G1/250-GUS, pCR16G1/EV-GUS and pCR16G1/H-GUS which are the plasmids of the present invention.

In the drawing, the black area is the non-stained region and the white area is the stained region, the vascular bundles are white in this drawing as the result of staining.

DESCRIPTION OF THE PREFERRED EMBODIMENTS

The present invention will be described in more detail.

In the present invention conventional gene engineering methods described, for example, in J. Sambrook, E. F. Frisch and T. Maniatis, Molecular Cloning, 2nd. Ed., published by Cold Spring Harbor Laboratory Press, 1989; D. M. Glober, DNA Cloning, published by IRL, 1985; and so on can be used.

First, description will be made to the promoter which is functional in plant cells comprising a nucleotide sequence (about 250 bp) of SEQ ID NO: 1.

The promoter may comprise a nucleotide sequence of SEQ ID NO: 2, which includes the nucleotide sequence of SEQ ID NO: 1.

The promoter may also comprise a nucleotide sequence (about 4 Kbp) having the following characteristics:

a. isolated and/or purified from carrot;
b. having restriction enzyme sites for XhoI (0 kb), XbaI (0.3 kb), EcoRV (2 kb), EcoRV (2.3 kb), EcoRI (3 kb), SmaI (3.6 kb) and HindIII (4 kb); and
c. containing a nucleotide sequence of SEQ ID NO: 2.

The promoters are preferably used for root-specific expression of a desired structural gene.

The "promoter which is functional in plant cells" herein mean a promoter having an ability of controlling expression of a protein in plant cells when a structural gene of the desired protein is ligated downstream of said promoter.

The promoters of the present invention as described above may be further modified by ligating to a nucleotide sequence such as:

a transcription-translation activating sequence formed by ligating -333 to -116 region of the Agrobacterium octopine synthesis gene with -318 to -138 region of the mannopine synthase gene, a transcription-translation activating sequence formed by ligating -318 to -213 region of the mannopine synthase gene with -333 to -116 region of the octopine synthesis gene (The Plant Journal, 7(4), 661–676 (1995)), a nucleotide sequence containing -343 to -91 of the cauliflower mosaic virus 35S promoter (Nature, 313, 810–812 (1985)), a nucleotide sequence containing -1099 to -205 of tomato ribulose-1,5-diphosphate carboxylase oxylase small subunit gene (rbc-3A) (Plant Cell, 1, 217–227 (1990)), a nucleotide sequence containing -902 to -287 of tobacco PR1a gene (Plant Cell, 2, 357–366 (1990)), or a nucleotide sequence containing -1300 to -195 of potato protease inhibitor gene (PI-II) (Plant Cell, 2, 61–70 (1990)).

The plasmid having anyone of the promoters of the present invention is usually constructed to have one or more cloning sites for inserting or excising a desired structural gene downstream of the promoter of the present invention.

The cloning site herein means a site which can be recognized and cleaved by a restriction enzyme used in the genetic engineering technology.

More specifically, the plasmid also comprises a chimera gene which is prepared by ligating a structural gene of a desired protein downstream of the promoter (the structural gene may be heterologous in relation with the promoter) in order to express a desired protein in plant cells.

Such chimera gene includes, for example, (1) a recombinant DNA gene having only the promoter of the present invention and the desired structural gene, and (2) a plasmid such as an extrachromosomal gene which contains said recombinant DNA gene and which is autonomously replicating physically independent of chromosomes of host and stably inheritable, and the like.

For enhancing the expression efficiency of the desired protein, plant cells are preferably transformed with a plasmid having the promoter of the present invention, the desired structural gene and a terminator which is functional in plant cells.

The "terminator which is functional in plant cells" means that the terminator has an ability of effectively terminating transcription of the desired structural gene in plant cells. Such a terminator usually exist in a genomic DNA region located downstream of a poly A sequence which usually exists downstream of poly (A) added-signal (made into a consensus sequence with AATAAA) present in a 3'-terminal non-translational region located downstream of a termination codon in structural genes of various proteins.

Examples of the terminator include a terminator which is functional in plant cells containing a nucleotide sequence of SEQ ID NO: 5, a terminator (NOS) in nopaline synthase gene derived from a plant gene, a terminator of garlic virus GV1, GV2 genes or the like.

Specific examples of the plasmid of the present invention having a cloning site include the plasmid shown in FIG. 1: pCR16G1/250-GUS, pCR16G1/EV-GUS and pCR16G1/H-GUS or the like.

The plasmid of the present invention can be prepared, for example, by the following process.

First, the promoter comprising a nucleotide sequence of SEQ ID NO: 1 is inserted in a multicloning site of a plasmid containing a terminator which is functional in plant cells, for example, pBI101 (manufactured by Clontech) (Jefferson et al., EMBO J., 6, 3901–3907 (1987)).

Then, an exogenote such as an existing marker gene, for example β-glucuronidase gene (hereinafter, referred to as GUS gene) is excised and said exogenote is replaced by a desired structural gene.

Alternatively, the promoter of the present invention, a desired structural gene and a terminator which are functional in plant cells are inserted in this order into a multicloning site of a binary vector, for example, pBIN19 (Nuc. Acid Res., 12, 8711–8721 (1984)).

Preferred examples of desired structural genes contained in the chimera gene of the present invention include useful genes capable of enhancing resistance against damage by disease and pest.

Examples of such a useful gene include a plant protection genes such as phenylalanine ammonia-lyase gene (PAL), chalcone synthase gene (CHS), chitinase gene (CHT), lysozyme gene, PR protein gene and the like, and disease resistance genes such as Pto gene, viral coat protein gene and the like.

Combat against pathogenic fungi localized in plant vascular bundle and pests taking nutrient from vascular bundle region or the like can be efficiently made by good expression of proteins encoded by these useful genes in vascular bundle of a plant utilizing the promoter of the present invention.

Further, since the promoter of the present invention enables expression of a desired protein particularly in vascular bundles of root, it is useful in (1) combat against pathogenic soil fungi and pests which are difficult to kill by chemicals and creation of a functional crop plant of which disease-susceptible root is provided with immunity or resistance against pathogenic fungi and pests; and (2) improving nutritive value of edible root plants, or creating of crop plant having an increased content of nutrients such as proteins.

Desired structural genes used for such purpose include, for example, BT (*Bacillus thuringiensis*) toxin protein gene, genes capable of enhancing resistance against damage by disease and pest as described above, genes capable of increasing content of various proteins in feeding crops such as storage protein gene including conglycinin gene, β-conglycinin gene of soybean and the like, genes capable of increasing methionine content or lysine content in feeding crops such as 2S albumin gene of Bertholletia excelsa Humb., 10 kDa and 15 kDa protein genes of corn and rice and the like, genes associated with biotin biosynthesis and are capable of increasing biotin content in feeding crop plant such as bioA, bioB, bioC, bioD, bioF or bioH enzyme genes of microorganism including *Escherichia coli* and the like, genes capable of increasing oxidation stability of lipids and of improving lipids by decrease of phospholipid and increase of oleic acid and linolenic acid such as genes for stearoyl-ACP-desaturase, acyl-ACP-thioesterase, 3-phosphate acyl transferase and the like, genes capable of increasing resistance against low temperature by increase of a ratio of unsaturated fatty acids such as acyl transferase gene, as well as genes which are herbicide resistance-associated genes and are capable of creating herbicide resistant crops such as genes of L-phosphonothrisine acetylase, (EPSP) synthase, PPO and the like.

Methods for introducing the chimera gene or the plasmid of the present invention include, for example, known methods such as Agrobacterium method (a method in which Agrobacterium, a soil bacterium, is infected to a plant tissue), electric introduction method (a method of electric introduction into protoplast: electroporation), direct introduction method by particle gun (a direct introduction method into plant tissue or cultivated cells: particle gun method) and the like. The plant cells transformed with promoter, chimera gene or plasmid of the present invention can be regenerated by a conventional plant tissue cultivating technique described, for example, in S. B. Gelvin, R. S. Schilperoot and D. P. S. Verma, Plant Molecular Biology, Manual, Kluwer Academic Publishers Press (1998); Valvekens et al., Proc. Natl. Acad. Sci., 85, 5536–5540 (1988) to give a plant or a part thereof originated from said plant cells.

Plants usable in the present invention include, for example, monocotyledons such as rice, maize, barley, wheat, onion and the like, dicotyledons including Leguminosae plant such as soybean, pea, bean, alfalfa and the like, Solanaceae plants such as tobacco, tomato, potato and the like, Cruciferae plants such as cabbage, rape, mustard and the like, Cucurbitaceae plants such as melon, pumpkin, cucumber and the like, Umbelliferae plants such as carrot, celery and the like, and Compositae plants such as lettuce and the like.

Plant cells and plants into which a desired structural gene has been introduced and expressing a protein encoded by the desired structural gene under control of the promoter of the present invention can be obtained in the above described manner.

The present invention further provides a protein which is isolated and /or purified from the root of carrot (*Daucus carota L.*) such as Kuroda Gosun. The protein has a molecular weight of 16 kD, of which amino acid sequence is shown in SEQ ID NO: 4. The nucleotide sequence of SEQ ID NO: 3 represents a nucleotide sequence of genomic DNA which contains both intron region and cDNA sequence coding for the amino acid sequence of SEQ ID NO: 4.

According to the present invention, creation of a carrot which is rich in a certain protein nutrient of interest becomes possible by introducing and expressing a gene encoding the protein into the root, for example, by the method described above utilizing the promoter of the present invention.

Similarly, the nutritive value of root crops can be improved by introduction and expression of a gene encoding a nutrient protein in the root. Examples of root crops include, for example, radish, turnip, sugar beet, burdock and the like.

Further, when a useful protein or its nucleotide sequence having a high homology with the protein or the nucleotide sequence encoding the protein of the present invention can be found in nucleotides data base such as EMBL, NBRF and so on, the nucleotide sequence that codes for the useful protein can be readily obtained by a conventional hybridization and cloning technique using the gene of the present protein, therefore the thus obtained gene can be introduced and expressed effectively by the present promoters.

Examples of such useful proteins include:

(1) a protein contributing to resistance against pathogens, which can provide a plant with resistance against pathogens and is useful for clarifying a mechanism of resistance against pathogen;

(2) a protein which acts as a plant hormone, and is expressed or induced in varying amount under influence of stress from the outside world or the like, of which expression control enables various improvements in cultivar utilizing response to stress or hormone;

(3) a protein associated with pollen allergy; controlled expression of the protein enables improvements in cultivar such that it forms improved pollen or controlled expression amount of pollen, which may result in no or low allergy; and (4) a protein associated with heat shock, which enables improvement in retaining or transport of plants by assisting holding of useful proteins.

Methods for isolating the promoter, terminator and protein of the present invention are illustrated below.

First, a genomic DNA is prepared from leaves, partially hydrolyzed with an appropriate enzyme and ligated to a vector arm derived from a λ-phage. This is packaged in vitro to form a phage particle, which is infected to *Escherichia coli* resulting in a plaque on an agar medium. This is recovered and a genomic library therefrom is used for gene screening. Methods for preparing genomic DNA include, for example, CTAB method described in M. Shure et al., Cell, 35, 325 (1983), the urea-phenol method described in S. O. Rogers and A. J. Bendich, Plant. Mol. Biol., 5, 69 (1985) and the like. As the λ-vector, for example, λFIX II, λEMBL3, λEMBL4, λDASH II available from Stratagene and the like can be used.

For in vitro packaging, for example, Gigapack Packaging Extract available from Stratagene can be used.

For selecting a genomic clone containing the nucleotide sequence of the promoter, the terminator or the protein of the present invention from the genomic library, an effective method is, for example, plaque hybridization using a probe formed by labelling a cDNA corresponding to a desired gene or a cDNA similar to the desired gene with RI or a fluorescent reagent or the like. The RI labelling can be effected, for example, using Random Labelling Kit available from Boeringer or Takara Shuzo or the like.

The fluorescent labelling can be effected, for example, using ECL Direct Nucleic Acid Labelling and Detection System available from Amersham or the like.

The genomic clone containing the nucleotide sequence of the promoter of the present invention, the terminator of the present invention or the protein of the present invention obtained by screening can be sequenced by subcloning into a plasmid vector of which DNA preparation or analysis can be conducted by a conventional method, in which commercially available pUC18, pUC19, pBluescript KS+, pBluescript KS– or the like are used to form a plasmid DNA, and a cycle sequence method in which Sanger method described in Sanger et al., J. Mol. Biol., 94, 441 (1975) and Sanger et al., Proc. Natl. Acad. Sci., 74, 5463 (1977) and PCR described in Saiki et al., Science, 230, 1350 (1985) can be used.

EXAMPLES

The present invention will now be described in more detail by means of Examples, which should not be construed as a limitation upon the scope of the present invention.

Example 1

Isolation of a gene of the protein of the present invention

A genomic library was made using a genomic DNA prepared from carrot leaves. The genomic library was screened using an already obtained cDNA fragment as a probe and two positive clones were obtained. The screening process is illustrated below:

Step 1: Preparation of a carrot genomic library (1) Preparation of a carrot genomic DNA In liquid nitrogen were triturated 10 g of carrot leaves at 6 weeks after seeding. The triturate was suspended in 5 ml of 2×CTAB solution (2% cetyl trimethyl ammonium bromide, 100 mM Tris-HCl buffer, pH 8.0, 20 mM EDTA, pH 8.0, 1.4 M NaCl, 1% polyvinylpyrrolidone) and incubated at 55° C. for 10 minutes. The same amount of chloroform/isoamyl alcohol (24:1) was added thereto and they were gently mixed at room temperature for 30 minutes, followed by centrifugation to separate upper and lower layers.

(a) To the upper layer was added the same amount of chloroform/isoamyl alcohol (24:1), and (b) to the lower layer was added the same amount of 1×CTAB solution (a double dilution of 2×CTAB solution with sterilized distilled water), and they were gently mixed at room temperature for 10 minutes, again followed by centrifugation, upon which the upper layers from both (a) and (b) were taken and mixed. To the mixture were added 1/10 amount of 10% CTAB solution (10% cetyl trimethyl ammonium bromide, 0.7 M NaCl) and the same amount of a precipitation buffer (2% cetyl trimethyl ammonium bromide, 50 mM Tris-HCl buffer, pH 8.0, 10 mM EDTA, pH 8.0) and they were gently mixed, followed by centrifugation. The obtained precipitates were suspended in 1 M NaCl-TE (1 M NaCl, 10 mM Tris-HCl buffer, pH 8.0, 1 mM EDTA, pH 8.0). The same amount of isopropanol was added thereto and they were gently mixed, followed by centrifugation. The obtained precipitates were rinsed with 70% ethanol, dried for a short time and suspended in TE. RNase was added thereto to a final concentration of 10 $\mu$g/ml and reacted at 37° C. for 30 minutes, upon which 1/4 amount of 4 M ammonium acetate and 2-fold amount of 100% ethanol were added and mixed to precipitate DNA. The obtained DNA was rinsed with 70% ethanol, dried for a short time and suspended in TE (10 mM Tris-HCl buffer, pH 8.0, 1 mM EDTA). The DNA solution was appropriately diluted, assayed for absorbance and electrophoresed in agarose gel to confirm production of about 350 $\mu$g of genomic DNA.

(2) Partial hydrolysis and insertion into $\lambda$-vector of the genomic DNA

A mixture of a 50 $\mu$g portion of the genomic DNA obtained as above and Sau3AI at a final concentration of 0.08 U/$\mu$l was incubated at 37° C. for 50 minutes to partially hydrolyze the DNA. A portion of the solution was fractionated by 0.5% agarose gel electrophoresis and it was confirmed that it was major in 20–50 kb DNA fragments. To this DNA solution was added an equal amount of phenol/chloroform/isoamyl alcohol (25:24:1) and they were sufficiently mixed, followed by centrifugation and separation of upper layer. The treatment with phenol/chloroform/isoamyl alcohol (25:24:1) was once repeated and the obtained solution was combined with 1/10 amount of 3 M sodium acetate and twice the amount of 100% ethanol, mixed well and the mixture was centrifuged after cooling at −80° C. for 10 minutes. Precipitates were rinsed with 70% ethanol, dried for a short time and suspended in TE. To this DNA solution were added 167 $\mu$M dATP, 167 $\mu$M dGTP and Klenon (Takara Shuzo) at a final concentration of 0.05 U/$\mu$l and the mixture was reacted at room temperature for 15 minutes. To this were added 1/10 amount of 10×STE and an equal amount of 1×STE and they were mixed. To the solution was added an equal amount of phenol/chloroform/isoamyl alcohol (25:24:1) and they were sufficiently mixed, followed by centrifugation and separation of upper layer. The treatment with phenol/chloroform/isoamyl alcohol (25:24:1) was once repeated and the obtained solution was combined with 1/10 amount of 3M sodium acetate and twice the amount of 100% ethanol, mixed well and the mixture was centrifuged after cooling at −80° C. for 10 minutes. Precipitates were rinsed with 70% ethanol, dried for a short time and suspended in TE. A reaction (50 mM Tris-HCl buffer, pH 7.5, 70 mM MgCl$_2$, 10 mM DTT) containing of a portion of this solution and 1 $\mu$g of $\lambda$/FIXII vector (Stratagene) was prepared. To this was added T$_4$ DNA ligase (Takara Shuzo) and the mixture was reacted overnight at 16° C.

(3) Packaging and Amplification of the library

The reaction solution from (2) was packaged using Gigapack II Gold Packaging Extract (Stratagene) and a genomic library having a bank size of 6×10$^4$. The host, *Escherichia coli* XL1-Blue MRA (P2), cultured overnight with shaking at 37° C. was suspended in 10 mM magnesium sulfate at a cell concentration: OD$_{600}$=0.5. To 200 $\mu$l of the cell suspension was added 10,000 pfu of phage and the mixture was scattered together with top agar preheated to 50° C. on a NZY plate, incubated at 37° C. for 8 hours and the propagated phage was suspended in SM buffer (50 mM Tris-HCl buffer, pH 7.5, 0.1 NaCl, 7 mM MgSO$_4$, 0.01% gelatine). The phage suspension was harvested and used for the following screening.

Step 2: Screening of the carrot genomic library (1) Preparation of a filter for screening On a NZY plate was scattered 50,000 pfu of phage and incubated at 37° C. for 8 hours. Onto this plate was overlapped a nylon filter Hybond-N (Amersham) and stood for 1 minute to adsorb the phage. Then the filter was treated with alkali to lyse the phage while DNA was bound to the filter, followed by treatment for neutralization (1.5 N NaCl, 0.5 M Tris-HCl, pH 8.0, 3 minutes×2 times). This was air-dried after washing with 2×SSC (300 mM NaCl, 30 mM citric acid) for 5 minutes, and irradiated with UV for 2 minutes to fix the DNA on the filter. The following hybridization reaction was carried out using 12 filters prepared in such manner.

(2) Plaque hybridization

The filters prepared above were placed in Hybripack, combined with a hybridization solution (6×SSC/1% SDS/100 $\mu$g/ml Calfthymus DNA) and incubated at 45° C. for 2 hours to effect hybridization. Using Random Labelling Kit (Boeringer Mannheim), 20–50 ng of cDNA fragment of the protein of the present invention was labelled with [$\alpha$-$^{32}$P.dDNA (0.74 MBq, Amersham) to make a probe. Into Hybripack were placed 3,000,000 cpm of the probe, 10 ml of the hybridization solution and the filter with sealing and they were incubated overnight at 45° C. After hybridization reaction, this was washed in 2×SSC/1% SDS at 45° C. for 10 minutes. The washing was repeated twice and this was rinsed with 2×SSC for a short time and then exposed to an imaging plate for 4 hours followed by analysis using BAS 2,000 (Fuji Film). Portions of 5 mm square of the plate corresponding to the sites where signal was detected were cut out and dipped in 500 $\mu$l of SM buffer to dissolve out the phage. Using this phage suspension, several hundreds pfu per plate of the phage was scattered and this was incubated at 37° C. for 8 hours. Filters were prepared as above from 2 plates per a signal and hybridization was carried out using cDNA fragment for the protein of the present invention labelled with [$\alpha$-$^{32}$P.dDNA ] as the probe. Phages were recovered from regions where the signals were detected by an image analyzer and the third screening was conducted in the same manner as above to isolate 2 phage clones expected to have the gene for the protein of the present invention. The following analysis was conducted for one of the above two.

Step 3: Subcloning and sequencing of the gene for the protein of the present invention (1) Preparation of phage DNA Into 1 liter Erlenmeyer's flask was placed NZYM medium (0.2% maltose was added to NZY liquid medium). To this was added *Escherichia coli* XL1-Blue MRA (P2) (manufactured by Stratagene, cultured overnight with shaking at 37° C., was added and the mixture was cultured overnight with shaking at 37° C. When OD$_{600}$ was 0.1, 5×10$^{10}$ of the phage was added and the culture was continued. The value of OD$_{600}$ was measured every hour and after lysis of *Escherichia coli* as the host was confirmed, 1.7 ml of chloroform was added and the mixture was stirred for 10 minutes. Phage DNA was prepared from 360 ml of the phage solution prepared in this manner using Lambda-trap (Clontech) to give about 21 g of the phage DNA.

(2) Characterization of the gene fragment for the protein of the present invention by Southern hybridization With each 0.5 U of restriction enzymes NotI, XbaI and SalI, respectively, a 50 ng portion of the phage DNA obtained in (1) was digested and the product was electrophoresed on 0.8% agarose gel to fractionate DNA fractions. After checking migration length of DNA in the gel by ethidium bromide staining, the gel was rinsed for a short time and shaken in 0.25 N HCl for 15 minutes. Then the gel was rinsed again with water for a short time and shaken in 1.5 N NaCl/0.5 N NaOH for 30 minutes. The gel was blotted to a Nylon filter Hybond-N (Amersham) (in 1.5 N NaCl/0.5 N NaOH, at 55 Atm for 1 hour) using Vacugene (Pharmacia). The blotted filter was washed with 2×SSC for 5 minutes, air-dried and irradiated for 2 minutes to fix the DNA onto the filter. The filter was packed with sealing in Hybripack together with the hybridization solution and incubated at 45° C. for 2 hours. In Hybripack were packed with sealing 3,000,000 cpm of the cDNA probe for the protein of the present invention prepared as described in Step 2, (2), 10 ml of the hybridization solution and filter and they were incubated overnight at 45° C. After the hybridization reaction, the filter was twice washed in 2×SSC/1% SDS at 45° C. for 10 minutes, rinsed with 2×SSC for a short time, exposed to an imaging plate for 2 hours and analyzed by BAS 2,000 (Fuji Film). As the result, it was demonstrated that the DNA fragment of 1.5 kb obtained by XbaI contained the gene for the protein of the present invention.

Figure 2:
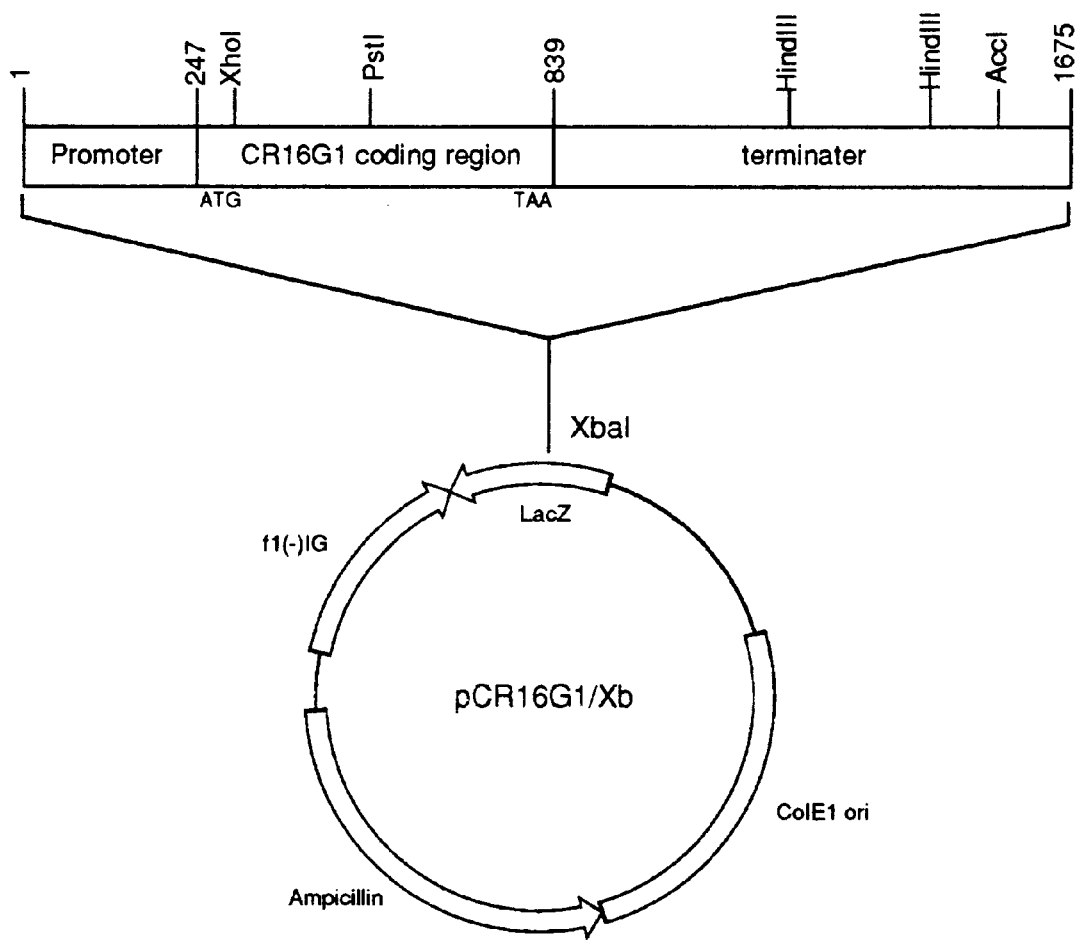
FIG. 2 shows pCR16G1/Xb which is a plasmid containing the gene of the protein of the present invention.

(3) Cloning of the DNA fragment containing the gene for the protein of the present invention After completely digesting 2 µg of pBluescript KS– vector (Stratagene) with 10 U of XbaI, the terminal of the product was de-phosphorylated with CIAP (Takara Shuzo). To the reaction solution was added an equal amount of phenol/chloroform/isoamyl alcohol (25:24:1) and they were sufficiently mixed, followed by centrifugation. The upper layer was separated, combined with 1/10 amount of 3M sodium acetate and twice the amount of 100% ethanol and mixed well. The mixture was centrifuged after cooling at −80° C. for 10 minutes. The obtained precipitates were rinsed with 70% ethanol, dried for a short time and suspended in TE. A 1 µg portion of phage DNA obtained in (1) was completely digested with 100 U of XbaI and the product was ligated to a 50·ng portion of pBluescript KS– vector prepared as above using a ligation kit (Takara Shuzo). An aliquot of the reaction solution was added to competent cells of *Escherichia coli* JM109 (Toyobo), transformed and the solution was spread on an LB plate containing 50 µg/ml of Ampicillin. After incubating overnight at 37° C., colony hybridization was carried out. Preparation of a filter, preparation of a probe, hybridization and washing were conducted in similar methods to those in (1) and (2), with the exception that hybridization and washing temperature was 65° C. AS the result of analysis by an image analyzer, many positive clones were obtained. From 18 clones among them, plasmid DNAs were prepared using QIA-prep spin column (Qiagen). The plasmid DNAs were digested with restriction enzyme XbaI which is suitable for cutting out the cloned DNA fragments and the product was fractionated with 0.8% agarose gel, analyzed and a clone, pCR16G1/Xb (see FIG. 2), containing a gene fragment (1.5 kb) of the protein of the present invention was selected. The selected clone was sequenced for total nucleotide sequence using TAq Dye Deoxy Terminator Cycle Sequencing Kit (ABI) and a fluorescence sequencer (ABI) (see SEQ ID NOs: 1, 3 and 5). As the result, it was demonstrated that the clone contained a 247 bp promoter region (the promoter of the present invention), a 592 bp coding region (the gene of the protein of the present invention) and a 836 terminator region (the terminator of the present invention).

Example 2

Homology of the protein of the present invention

The nucleotide sequence of the gene of the protein of the present invention as determined in Example 1 (see SEQ ID NO: 3) and the amino acid sequence of the protein of the present invention encoded by it (see SEQ ID NO: 4) were searched in data bases EMBL and NBRF. As the result, it was revealed that the gene of the protein of the present invention and the amino acid sequence encoded by it had a high homology with pollen allergen proteins in celery, white birch and the like, PR proteins associated with resistance to pathogen in parsley, potato and the like, proteins induced by stress from outer world in pea, soybean and the like (see FIG. 3). The highest homology was seen in APIg1 in celery, PR1-3 and PR1-1 which are PR proteins in parsley, contained in Umbelliferae plants which include carrot. Also, a relatively high homology was observed with mRNA of HSP60 which is a mouse heat shock protein.

Example 3

Analysis of expression pattern of the gene of the protein of the present invention by Northern hybridization Total RNAs were extracted from each 2 g of flower, leaf and root of carrot, respectively, using Isogen (Nippon Gene), and further, about 40 µg of mRNA was prepared using Oligotex-dT30 (Takara Shuzo). A 5 µg portion of mRNA was fractionated with 1.2% modified agarose gel electrophoresis and blotted to a Nylon filter Hybond-N (Amersham) in 10×SSC by the capillary blotting method. After blotting, the filter was air-dried and baked at 80° C. for 2 hours to fix the DNA. The filter was dipped in a prehybridization solution and incubated at 45° C. for 2 hours. Using pCR16G1/Xb as a template and primers that amplify the 3'-non-coding region which have the following sequences:

5'-GCTGA ACTTT CCACC GTGTT-3' (SEQ ID NO: 6) and

5'-GACAT CTCAT AGTTG AGACT C-3' (SEQ ID NO: 7),

PCR reaction (30 cycles in which 1 cycle consisted of treatments: 94° C., 1 minute; 55° C., 1 minute; 72° C., 1 minute) was conducted. In this reaction, a label was introduced by adding [α-$^{32}$P.dCTP], and using the product as the probe, the hybridization was conducted in a manner similar to that in Step 3, (2). The product was analyzed by an image analyzer and it was confirmed that the gene for the protein of the present invention was highly transcribed in root.

Example 4

Obtaining the promoter of the present invention

Figure 4:
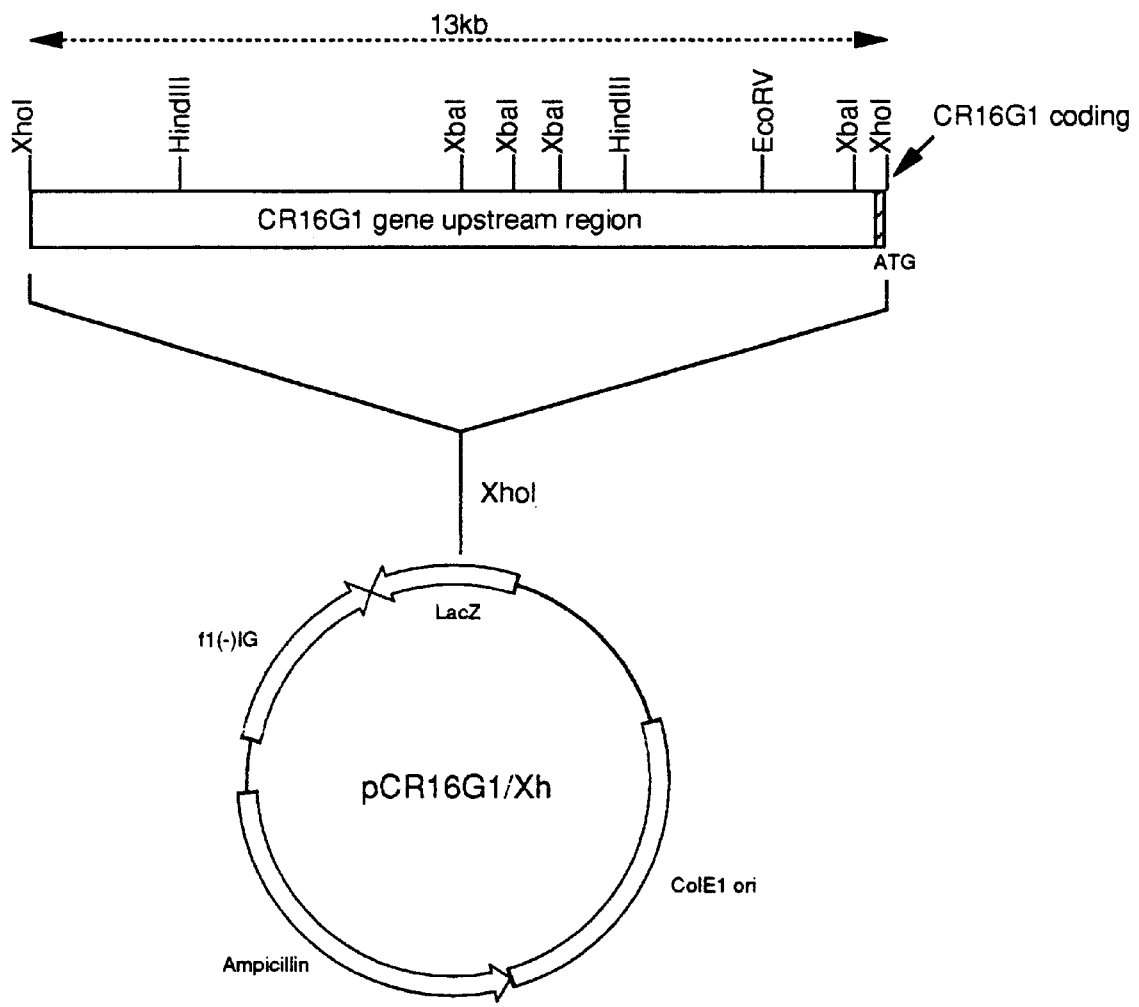
FIG. 4 shows pCR16G1/Xh which is a plasmid of the present invention (a plasmid containing a part of the gene of the protein of the present invention and the promoter of the present invention).

Using a ligation kit (Takara Shuzo), 50 ng of pBluescript KS– vector completely digested with XhoI and dephosphorylated at the terminal was ligated with 1 µg of a phage genomic clone DNA completely digested with XhoI. An aliquot of the reaction solution was added to 100 µl of competent cells of *Escherichia coli* JM109 (Toyobo), transformed and the solution was spread on an LB plate containing 100 µg/ml of Ampicillin. After incubating overnight at 37° C., a plasmid was prepared from the growing clone using QIA-prep spin (Qiagen) and a region of several hundreds bp at the terminal of contained insert DNA was sequenced. As the result, pCR16G1/Xh (see FIG. 4), which is a clone containing a part of the coding region of the gene of the protein of the present invention and a 13 kb upstream region was obtained. The promoter region (2 kb) of the gene of the protein of the present invention contained therein was sequenced using TAq Dye Deoxy Terminator Cycle Sequencing Kit (ABI) and a fluorescence sequencer (ABI) (see SEQ ID NO: 1).

Example 5

Construction of the plasmids of the present invention (1) Preparation of the promoter (247 bp) of the present invention Using a sequence located inside the vector and a sequence located several tens bps upstream of ATG of the gene of the protein of the present invention as primers, which have the following sequences:

5'-GTAAA ACGAC GGCCA GT-3' (SEQ ID NO: 8) (Made by Takara Shuzo) and

5'-GGGCT AGCGA CCTTT AGAAT GTTTT TGC-3' (SEQ ID NO: 9), and pCR16G1/Xb as a template, PCR reaction (40 cycles in which 1 cycle consisted of treatments: 94° C., 1 minute; 40° C., 2 minutes; 72° C., 3 minutes) was conducted to amplify the DNA fragment containing the promoter of the present invention (247 bp). As the upstream primer of the gene ATG of the protein of the present invention, a synthesized primer having a recognition site for the restriction enzyme NheI at the 5' terminal was used. To the reaction product was added an equal amount of chloroform/isoamyl alcohol (24:1), the obtained solution was centrifuged and the upper layer was separated. To this was added 1/10 amount of 3M ammonium acetate and twice the amount of 100% ethanol and mixed. The mixture was centrifuged to give precipitates, which was completely hydrolyzed with restriction enzymes XbaI and NheI and then fractionated by 4% polyacrylamide electrophoresis. The gel was cut out such that a DNA fragment having the desired length was contained and the DNA fragment was harvested according to the method described in Molecular Cloning. Thus, the gel was finely cut and the sections were dipped in a extraction buffer, incubated at 37° C. for 5 hours and gel sections were removed by centrifugation. The solution was combined with twice the amount of 100% ethanol and the mixture was cooled on ice. Precipitates obtained upon centrifugation was suspended in TE. To this were added 1/10 amount of 3M ammonium acetate and twice the amount of 100% ethanol and ethanol precipitation was carried out as above. The obtained precipitates were re-suspended in TE and subjected to 4% polyacrylamide electrophoresis to check the concentration of the DNA fragment, which was used for the construction of the plasmid of the present invention.

(2) Construction of the plasmid (pCR16G1/250-GUS) of the present invention

The promoter of the present invention (247 bp) prepared as described in Example was ligated to a binary vector pBI101 (Clontech) which had been cut with XbaI and treated with CIAP and the resulting was used to infect Escherichia coli JM109 competent cells to obtain transformants. Clones grown on an LB plate containing 50 μg/ml of kanamycin was selected. A plasmid DNA was prepared therefrom and cut with a restriction enzyme to give a candidate clone containing the promoter of the present invention (247 bp). The clone was sequenced using a synthetic primer of which sequence is the same as that located inside the coding region of GUS gene and which has the following sequence:

5'-TCACG GGTTG GGGTT TCTAC-3' (SEQ ID NO: 10).

Figure 5:
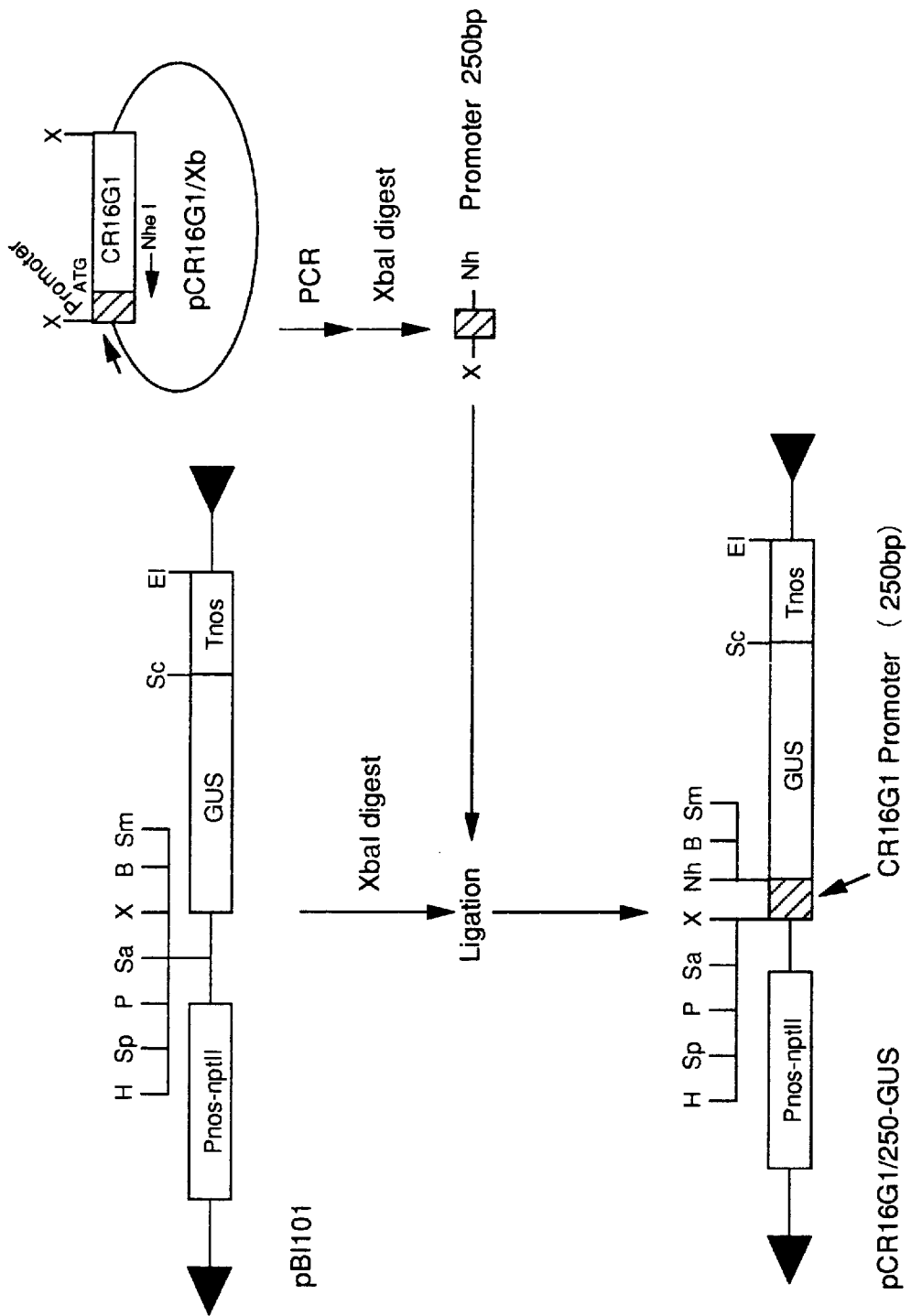
FIG. 5 shows steps for constructing pCR16G1/250-GUS, which is a plasmid of the present invention, from pBI101.

It was confirmed that no nucleotide substitution was occurred in the 247 bp promoter region by Taq polymerase (see FIG. 5).

Figure 6:
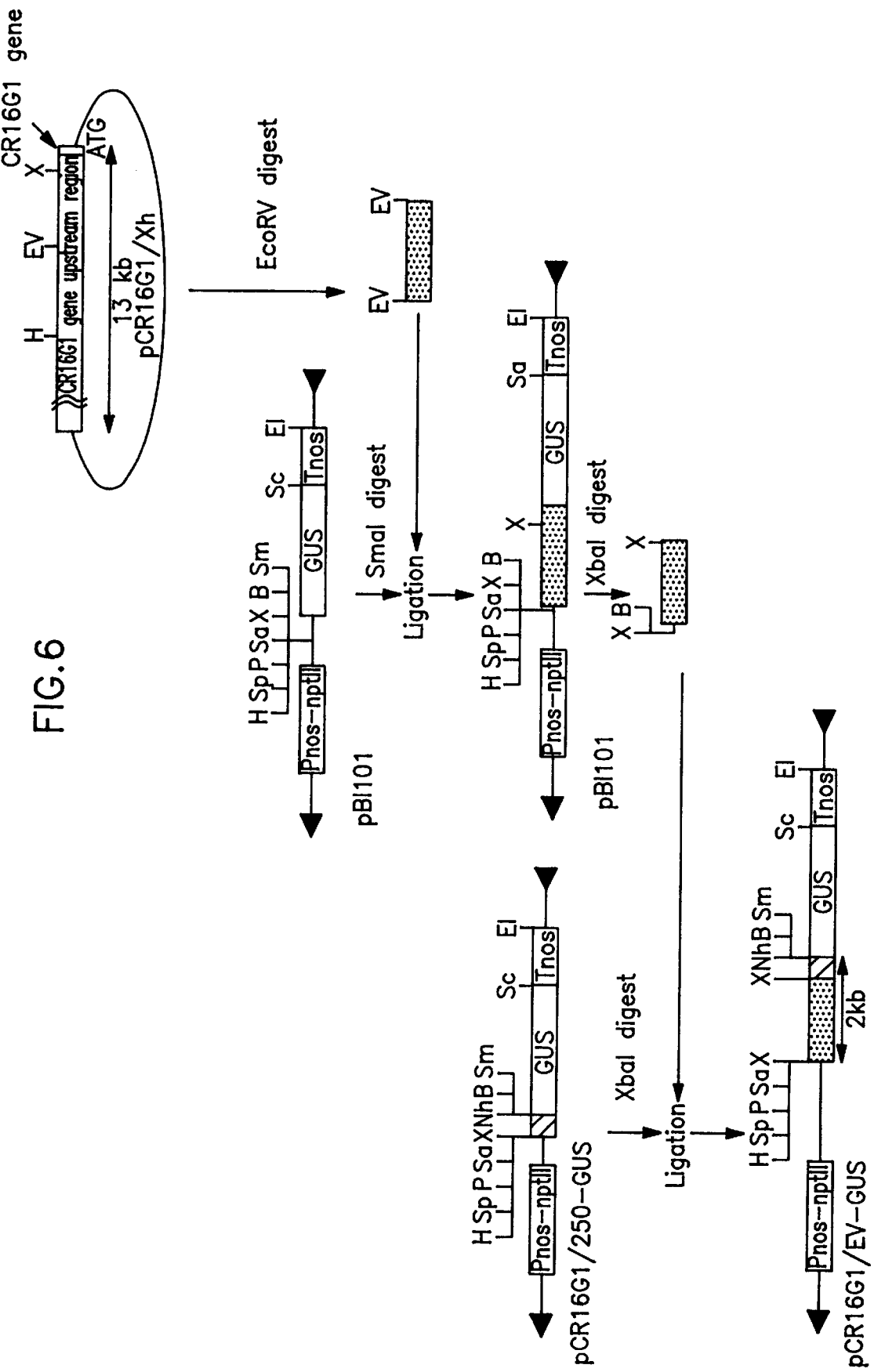
FIG. 6 shows steps for constructing pCR16G1/EV-GUS, which is a plasmid of the present invention, from pBI101 and pCR16G1/250-GUS.

(3) Construction of the (expression) plasmid (pCR16G1/EV-GUS) of the present invention pCR16G1/XhoI was cut by EcoRV and the resulting fragment was fractionated by 0.8% agarose gel electrophoresis. A band corresponding to a DNA fragment containing the promoter of the present invention (247 bp) was cut out and the DNA fragment was recovered using glass beads (Bio-Rad). Concentration of DNA in the obtained DNA fragment was checked by 0.8% agarose gel electrophoresis and the DNA was ligated to a binary vector pBI101 digested with a restriction enzyme SmaI. Escherichia coli JM109 competent cells were infected with the fragment to transform the cells. A clone grown on an LB plate containing 50 μg/ml of kanamycin was selected. A plasmid DNA was prepared from the grown clones and orientation of the insert was investigated by restriction enzyme digestion. A clone having an insert in normal orientation was taken. This clone was mass-cultured and the plasmid DNA was mass-produced using Qiagen Tip-500 column (Qiagen). The plasmid DNA was digested with XbaI, fractionated by 0.8% agarose gel electrophoresis and 1.75 kb DNA fragment (containing upstream region of the 247 bp) was recovered in a manner similar to that described above. This was treated with CIAP and ligated to pCR16G1/250-GUS that had been digested with a restriction enzyme XbaI (connection site of NheI and XbaI became uncleavable). The resulting fragment was used to infect Escherichia coli JM109 competent cells to obtain transformant, and a plasmid was prepared from kanamycin resistant clone. By restriction digestion, it was confirmed that the clone contained the promoter of the present invention (2 kb). Further, using a synthetic primer having the same sequence as that located inside the GUS coding region, which have the following sequence:

5'-TCACG GGTTG GGGTT TCTAC-3' (SEQ ID NO: 10), the promoter region was sequenced and the structure of about 500 bp upstream of ATG in GUS gene was characterized (SEQ ID NO: 2, see FIG. 6).

Figure 7:
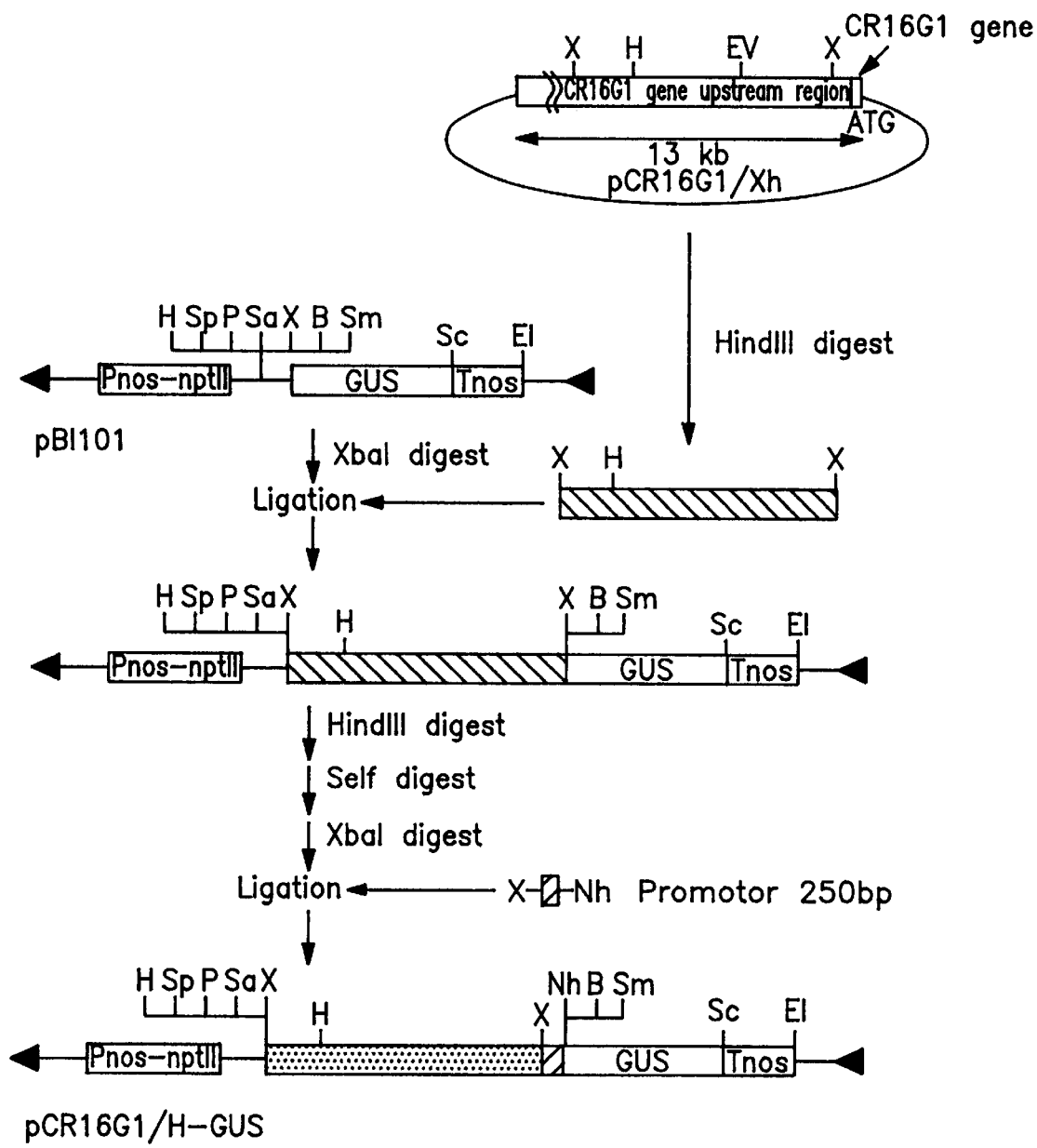
FIG. 7 shows steps for constructing pCR16G1/H-GUS, which is a plasmid of the present invention, from pBI101.
Figure 8:
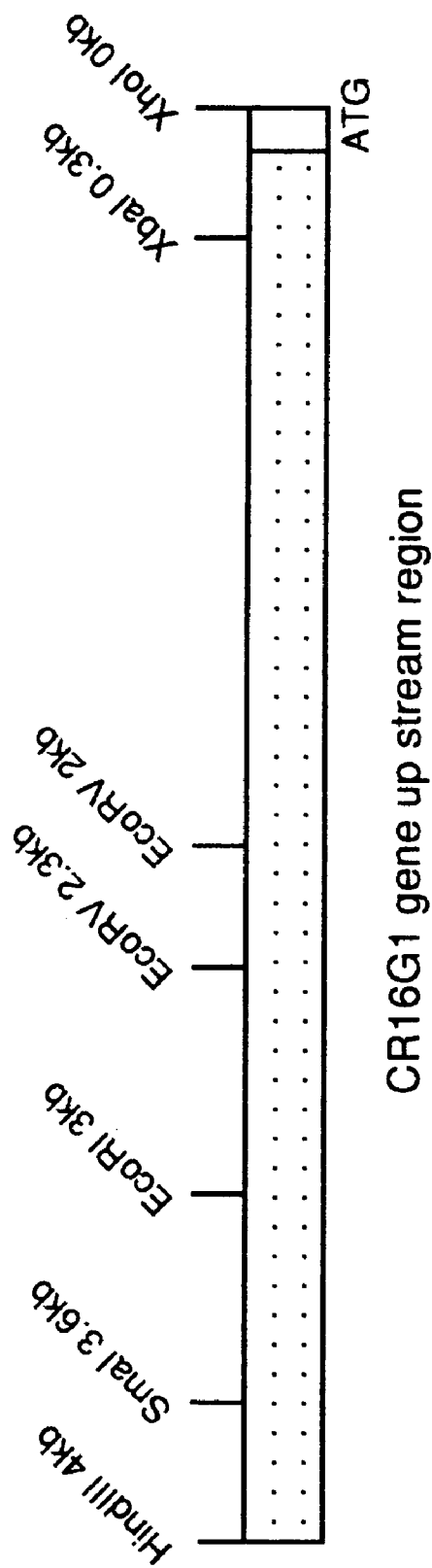
FIG. 8 shows a promoter of the present invention, which has a region (about 4 Kbp) having restriction sites for XhoI (0 kb), XbaI (0.3 kb), EcoRV (2 kb), EcoRV (2.3 kb), EcoRI (3 kb), SmaI (3.6 kb) and HindIII (4 kb).

(4) Construction of the plasmid (pCR16G1/H-GUS) of the present invention pCR16G1/XhoI was cut by XbaI and a DNA fragment containing 5 kb sequence located upstream of the gene ATG of the protein of the present invention was recovered in the same manner as (3) above. The resulting fragment was ligated to a binary vector pBI101 that had been digested with a restriction enzyme XbaI. The product was used to infect competent cells to obtain transformants. A clone having an insert in normal orientation was obtained. This clone was further digested with HindIII, self-ligated, transformed and it was confirmed that the obtained clone had only one HindIII restriction site. The plasmid DNA was digested with XbaI and ligated to the promoter of the present invention (247 bp) as described above. A plasmid was prepared using this clone having the promoter of the present invention (247 bp) inserted in the normal orientation. Using a synthetic primer having the same sequence as that located inside the GUS coding region, which has the following sequence:

5'-TCACG GGTTG GGGTT TCTAC-3' (SEQ ID NO: 10), the plasmid was sequenced in the same manner as above and the structure of about 500 bp upstream of ATG in GUS gene was characterized (see FIGS. 7 and 8). This allowed to confirm that the structure at and around the ligation site was not changed.

Example 6
Production of cells and a plant of the present invention

Production of a transgenic plant was performed according to the method described in S. B. Gelvin, R. A. Schileroort and D. P. S. Verma, Plant Molecular Biology/Manual (1988) (Kliwer Academic Publishers; Valvekens et al., Proc. Natl. Acad. Sci., 85, 5536–5540 (1988)).

Agrobacterium LBA4404 strain cultured overnight in YEB medium at 30° C. with shaking was subcultured to a fresh YEB medium and the cultivation was continued until $OD_{600}$ was 0.6. The following procedure was conducted in a cooled room. Cells were collected from the culture by centrifugation, suspended in cooled distilled sterile water and collected by centrifuging again. This washing operation was twice repeated and a similar operation was performed replacing distilled sterile water by 10% glycerol solution. The obtained cells were suspended in 10% glycerol so as to obtain finally at 400 times the concentration. To this competent cells were introduced the three Ti plasmid expression vectors (hereinafter, referred to as pCR16G1/250-GUS, pCR16G1/EV-GUS and pCR16G1I/H-GUS) constructed as described above by electroporation method and selected on YEB plate containing 50 μg/ml of kanamycin. Plasmid DNAs were prepared from grown kanamycin-resistant clones by alkali-SDS method, and it was confirmed by 0.8% agarose gel electrophoresis and ethidium bromide staining that the Ti expression vectors were introduced. The strains of Agrobacterium (pCR16G1/250-GUS/LBA4404, pCR16G1/EV-GUS/LBA4404 and pCR16G1/H-GUS/LBA4404) were cultured with shaking in YEB liquid medium at 30° C. over 2 nights.

After non-symbiotic seeding, roots of Arabidopsis grown at 23° C. for 2–3 weeks that were cut into about 1 cm were incubated on CIM plates for 2 days, dipped in a culture of Agrobacterium (pCR16G1/250-GUS/LBA4404, pCR16G1/EV-GUS/LBA4404 or pCR16G1/H-GUS/LBA4404) cultivated with shaking at 30° C. over 2 nights and incubated again on CIM plates. After 2 days, the sections of root were transferred to SIMC medium and, further 2 days later, they were subcultured to SIMCK medium. About 1 month after, regenerated shoot was cut off and transplanted to RIM medium to cause rooting. A rooted individuals were planted in soil or rock wool, grown in an air-conditioned room to obtain self-propagated seeds.

Sections of aseptically incubated tobacco leaves were dipped in MS medium. Aliquot of 30° C.-overnight culture of Agrobacterium strains (pCR16G1/250-GUS/LBA4404, pCR16G1/EV-GUS/LBA4404, pCR16G1/H-GUS/LBA4404) was added to the medium and co-incubation was continued at 25° C. for 2 days in the dark. Thereafter, the sections of leaves were washed with MS liquid medium and placed on MS-NBCK medium. They were stationarily cultured at 25° C. for about 1 month in the light, a regenerated shoot was cut off from the section of leaf and transplanted to MS-CK medium. About 1 month later, rooted individuals were planted in soil, grown in a green house and self-propagated seeds were obtained.

Example 7
Confirmation amplification of introduced gene in the plant of the present invention The seeds of transgenic Arabidopsis obtained in Example 6 were sterilized with 1% hypochlorous acid for 5 minutes, washed 3–5 times with sterilized distilled water and then non-symbiotically germinated in MS medium containing 20 μg/ml kanamycin. From an individual exhibiting kanamycin resistance, 4–5 rosette leaves were taken and the genomic DNA was prepared from them by CTAB method.

Using 50 ng of this DNA as a template and a sequence located inside the GUS gene which is a reporter gene and a sequence located around 250 bp upstream of ATG in GUS gene (inside the promoter of the present invention) as primers, which have following sequences:

5'-TCTGC ATCGG CGAAC TGATC-3' (SEQ ID NO: 11) and

5'-ACAAA CACAG CACTA ACTTT TC-3' (SEQ ID NO: 12)

and further, using a sequence located inside GUS gene and a sequence located inside NOS terminator as primers, which have the following sequences:

5-ACATG TGGAG TGAAG AGTAT C-3' (SEQ ID NO: 13)and

5'-CATGC TTAAC GTAAT TCAAC AG-3' (SEQ ID NO: 14),

PCR reactions (40 cycles in which 1 cycle consisted of treatments: 94° C., 1 minute; 55° C., 2 minutes; 72° C., 3 minutes) were conducted, then a portion of PCR product was fractionated by 0.8% agarose gel electrophoresis. Thus amplification of the desired DNA fragment (introduced gene) was confirmed.

Also, for the transgenic tobacco, the seeds were sterilized with 2.5% hypochlorous acid/0.002% Triton X-100 for 5 minutes, washed 4–5 times with sterilized water. The seeds were non-symbiotically germinated in MS medium containing 100 μg/ml kanamycin. Using an individual among those exhibiting kanamycin resistance, the genomic DNA was prepared by CTAB method: the same method as that for Arabidopsis, i. e. using an individual among those exhibiting kanamycin resistance, the genomic DNA was prepared by CTAB method. Using 50 ng of this DNA fragment as a template and a sequence located inside the GUS gene and a sequence located around 250 bp upstream of ATG in GUS gene (inside the promoter of the present invention), which have the following sequences:

5'-TCTGC ATCGG CGAAC TGATC-3' (SEQ ID NO: 11) and

5'-ACAAA CACAG CACTA ACTTT TC-3' (SEQ ID NO: 12)

and further, using a sequence located inside the GUS gene and a sequence located inside NOS terminator as primers, which have following sequences:

5'-ACATG TGGAG TGAAG AGTAT C-3' (SEQ ID NO: 13) and

5'-CATGC TTAAC GTAAT TCAAC AG-3' (SEQ ID NO: 14),

PCR reactions (40 cycles in which 1 cycle consisted of treatments: 94° C., 1 minute; 55° C., 2 minutes; 72° C., 3 minutes) were conducted, then a portion of PCR product was fractionated by 0.8% agarose gel electrophoresis and amplification of the desired DNA fragment (introduced gene) was confirmed.

Example 8
Confirmation of expression pattern of the introduced gene

Measurement of GUS staining and GUS activity in the leaf and root of seeding from the plant of the present invention (containing the plasmids of the present invention: pCR16G1/250-GUS, pCR16G1/EV-GUS, pCR16G1/H-GUS and, as controls, pBI121 (manufactured by Clontech), pBI101) obtained in Example 6 was conducted according to the method described in Plant Mol. Bio. Rep., 5, 387–405 (1987).

The measurement of GUS activity was carried out by the fluorescence method using 4-methylumbelliferyl-glucuronic acid as the substrate and that of activity staining was carried out by determining deposition of a blue pigment (indigotin) using 5-bromo-4-chloro-3-indolyl-β-D-glucuronic acid (X-Gluc) as the substrate.

(1) GUS staining

Figure 9:
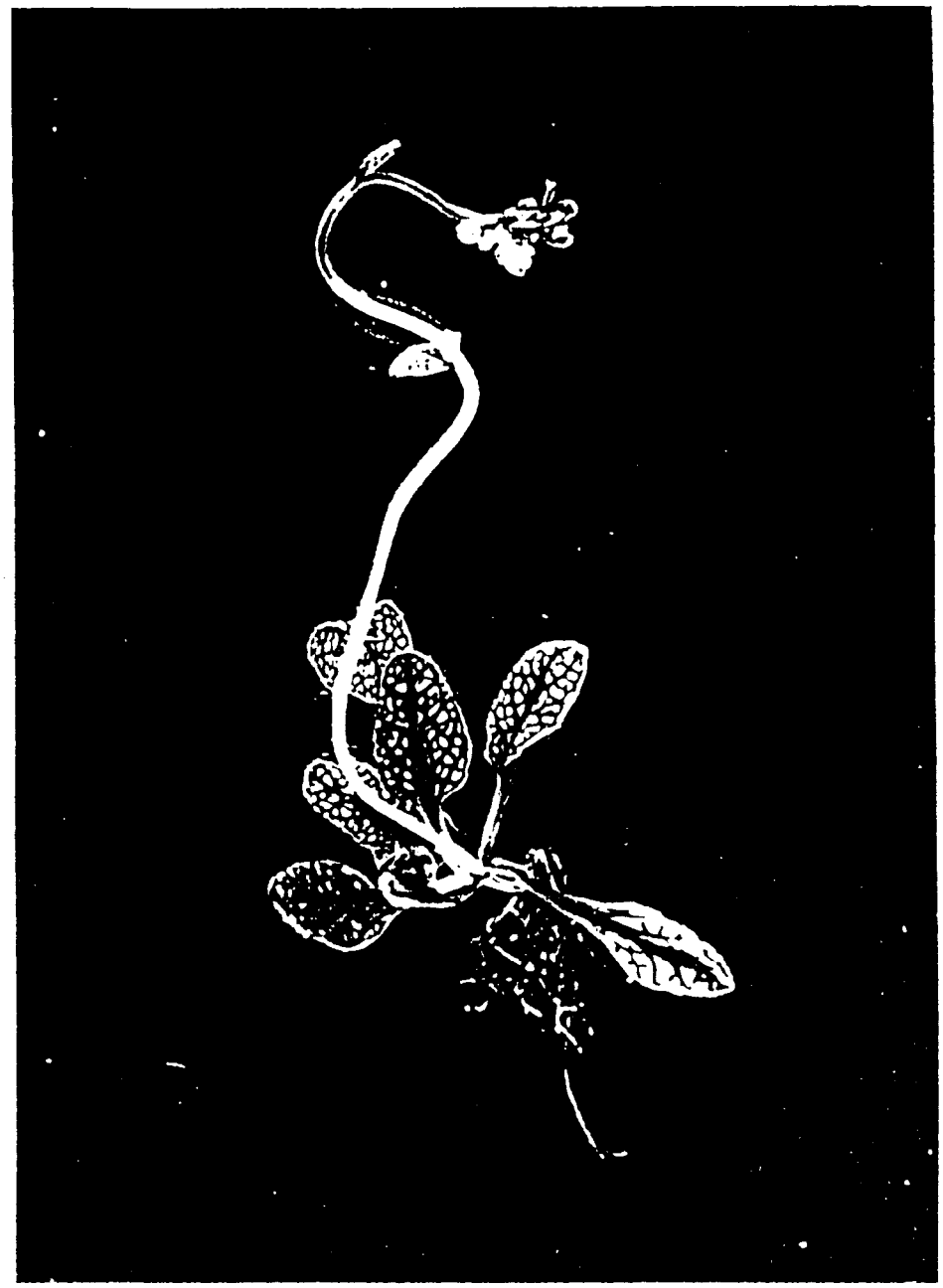
FIG. 9 shows a visualization (showing morphology of an organism) by staining indicating high expression of the desired protein in the vascular bundles of a plant owing to the promoter of the present invention. The vascular bundles are white in this drawing as the result of staining. In the drawing, the black area is the non-stained region and the white area is the stained region.
Figure 10:
FIG. 10 shows a visualization (showing morphology of an organism) by staining indicating high expression of the desired protein in the vascular bundles of a plant owing to the promoter of the present invention.

The seeds of transgenic Arabidopsis were non-symbiotically germinated in MS medium containing 20 μg/ml kanamycin and individuals exhibiting kanamycin resistance were grown for 3 weeks. The plants were pulled out taking care not to damage the root, dipped in GUS staining solution (1 mM X-Gluc, 0.5 mM $K_3Fe(CN)_6$, 0.5 mM $Fe_4Fe(CN)_6$, 0.3% Triton X-100) and incubated overnight at 37° C. After the reaction was completed, they were decolorized by washing several times with 100% ethanol and staining pattern was observed. The results confirmed that the product of the introduced gene was highly expressed in vascular bundles, particularly in vascular bundles of the root, in every plant of the present invention (see FIGS. 9 and 10). The intensity of expression was the strongest in the plant of the present invention in which pCR16G1/H-GUS was introduced (see Table 1).

The seeds of transgenic tobacco were non-symbiotically germinated in MS medium containing 100 μg/ml kanamycin and individuals exhibiting kanamycin resistance were pulled out after 1 or 3 weeks or 1 month. They were dipped in GUS staining solution and incubated overnight at 37° C. Then, they were decolorized with 100% ethanol and staining pattern was observed. The results confirmed the similar tendency to that of the expression in transgenic Arabidopsis. It was also confirmed that the staining became stronger with the progress of growth stage.

(2) Measurement of GUS activity

The seeds of transgenic tobacco were non-symbiotically germinated in MS medium containing 100 μg/ml kanamycin and incubated at 25° C. for 1 month. To 0.8 g of root and 0.5 g of leaves respectively placed in a mortar was added 1 ml or 0.5 ml, respectively, of an extraction buffer (50 mM phosphate buffer, pH 7.0, 10 mM EDTA, 0.1% Triton X-100, 0.1% Sarcosyl, 10 mM mercaptoethanol) and they were triturated with an appropriate amount of sea sand. The triturate was transferred to an Eppendorff tube, centrifuged and the supernatant was taken out. Aliquots of 10–70 μl were added to 500 ml of a reaction substrate solution (50 mM phosphate buffer, pH 7.0, 10 mM EDTA, 0.1% Triton X-100, 0.1% Sarcosyl, 10 mM mercaptoethanol, 1 mM 4-methylumbelliferyl-β-D-glucuronide) and reacted at 37° C. After reacting, 100 μl aliquot samples were taken out and immediately mixed with 900 μl reaction quenching solution (0.2 M sodium carbonate solution). The treated samples were assayed by a spectrophotofluorometer (model F-2000, Hitachi Seisakusho). GUS activity was calculated from the results of measurement and protein concentrations in extracts from leaves and root. Determination of protein concentration was carried out by a method using Protein Assay Reagent available from Bio-Rad. As the result, the highest activity was detected in the root, in the plant of the present invention (see Table 2).

TABLE 1

Comparison of GUS activity in root of transgenic tobacco plants into which various promoters were introduced:

| Introduced Gene | Ratio of GUS Activity |
| --- | --- |
| pCR16G1/250-GUS | 121 |
| pCR16G1/EV-GUS | 401 |

TABLE 1-continued

Comparison of GUS activity in root of transgenic tobacco plants into which various promoters were introduced:

| Introduced Gene | Ratio of GUS Activity |
| --- | --- |
| pCR16G1/H-GUS | 305 |
| pBI101 (no promoter-GUS) | 100 |

*The ratio is calculated taking GUS activity in root of pBI101 as 100.

TABLE 2

Comparison of GUS activity in various tissues of transgenic tobacco plants into which various promoters were introduced:

| Introduced Gene | Ratio of GUS Activity | |
| --- | --- | --- |
| | Leaf | Root |
| pCR16G1/250-GUS | 1 | 56 |
| pCR16G1/EV-GUS | 1 | 34 |
| pCR16G1/H-GUS | 1 | 245 |
| pBI121 (35S promoter-GUS) | 1 | 4 |

*The ratio is calculated taking GUS activity in leaf as 1.

Composition of media used in Examples are shown below:

(1) Media for tobacco plants a) MS agar medium

Into 1 liter of distilled water were dissolved 4.4 g of Murashige and Skoog (Flow Laboratories) and 30 g of sugar. The solution was adjusted to pH 5.8 with 1 M KOH, combined with 3 g of gellan gum (Wako Pure Chemical) and sterilized in an autoclave.

b) MS-NBCK agar medium

This medium was prepared by adding 0.1 μl/mg of 1-naphthaleneacetic acid (NAA), 1.0 μg/ml of 6-benzylaminopurine (BA), 20 μg/ml of kanamycin and 300 μg/ml of claforan to MS agar medium.

c) MS-CK agar medium

This medium was prepared by adding 100 μg/ml of kanamycin and 300 μg/ml of claforan to MS agar medium.

(2) Media for Arabidopsis a) MS agar medium

Into 1 liter of distilled water were dissolved 4.4 g of Murashige and Skoog (Flow Laboratories) and 20 g of sugar. The solution was adjusted to pH 6.3 with 1M KOH, combined with 2 g of gellan gum (Wako Pure Chemical) and sterilized in an autoclave.

b) CIM agar medium

This medium was prepared by adding 0.5 μg/ml of 2,4-dichlorophenoxyacetic acid (2,4-D) and 0.05 μg/ml of kinetin to MS agar medium.

c) SIMC agar medium

This medium was prepared by adding 5 μl/mg of [2-isopentenyl.adenine (2-Pi), 0.15 μg/ml of indolacetic acid (IAA) and 300 μg/ml of claforan to MS agar medium.

d) SIMCK agar medium

This medium was prepared by adding 20 μl/mg of kanamycin to SIMC medium.

(3) Media for bacteria and phages a) L medium

Into 1 liter of distilled water are dissolved 10 g of Bactotripton (Difco), 5 g of Bacto yeast extract (Difco) and 10 g of NaCl. The solution is adjusted to pH 7.0 with 5 M NaOH and sterilized in an autoclave. For plate medium, 15 g of agar is added.

b) YEB medium

Into 1 liter of distilled water are dissolved 5 g of Bacto beef extract (Difco), 1 g of Bacto yeast extract (Difco), 5 g of polypeptone, 5 g of sugar and 0.2 ml of 10 M NaOH. The solution is sterilized in an autoclave. Thereafter, 0.2 ml of filter-sterilized 1M $MgSO_4$ is added on use. For plate medium, 15 g of agar is added.

c) NZY medium

Into 1 liter of distilled water are dissolved 5 g of yeast extract, 10 g of NZ amine, 5 g of NaCl and 2 g of $MgSO_4 \cdot 7H_2O$. The solution is adjusted to pH 7.5 with 5M NaOH and sterilized in an autoclave. For plate medium, 15 g of agar (Difco) is added.

d) Top agar

This medium is prepared by adding 0.7 g of Agarose-II (Dojin) to 100 ml of NZY medium.

Effect of the Invention

By utilizing the promoter of the present invention, high expression of a desired protein in plant vascular bundles (particularly in vascular bundles in root) became possible.

What is claimed:

1. An isolated promoter which is functional in plant cells comprising a nucleotide sequence of about 250 bp of SEQ ID NO: 1.

2. An isolated promoter which is functional in plant cells comprising a nucleotide sequence of about 2 Kbp of SEQ ID NO: 2.

3. A promoter which is functional in plant cells, said promoter comprising a nucleotide sequence of about 4 Kbp having the following characteristics:
   a. isolated and/or purified from carrot;
   b. having restriction enzyme sites for XhoI (0 kb), XbaI (0.3 kb), EcoRV (2 kb), EcoRV (2.3 kb), EcoRI (3 kb), SmaI (3.6 kb) and HindIII (4 kb); and
   c. containing a nucleotide sequence of SEQ ID NO: 2.

4. A plasmid comprising a promoter as defined in claim 1.

5. A plasmid comprising a promoter as defined in claim 2.

6. A plasmid comprising a promoter as defined in claim 3.

7. A chimeric gene comprising a promoter as defined in claim 1 and a desired structural gene.

8. A chimeric gene comprising a promoter as defined in claim 2 and a desired structural gene.

9. A chimeric gene comprising a promoter as defined in claim 3 and a desired structural gene.

10. A plasmid comprising a chimeric gene as defined in claim 7.

11. A plasmid comprising a chimeric gene as defined in claim 8.

12. A plasmid comprising a chimeric gene as defined in claim 9.

13. A plasmid selected from the group consisting of pCR16G1/H-GUS, pCR16G1/EV-GUS and pCR16G1/250-GUS.

14. A microorganism containing the plasmid according to claim 4, 5 or 6.

15. A microorganism containing the chimeric gene according to claim 7, 8 or 9.

16. A plant cell wherein the expression of a desired protein is under control of the promoter of claim 1, 2 or 3.

17. A plant cell containing the chimeric gene of claim 7, 8 or 9.

18. A plant into which the promoter of claim 1, 2 or 3 has been introduced, wherein a desired protein is expressed.

19. A plant containing the chimeric gene of claim 7, 8 or 9.

20. A process for preparing a chimeric gene which comprises ligating a desired structural gene downstream of the promoter of claim 1, 2 or 3.

21. An isolated terminator which is functional in plant cells comprising a nucleotide sequence of SEQ ID NO: 5.

* * * * *